United States Patent [19]

Hershman et al.

[11] 4,264,776

[45] Apr. 28, 1981

[54] PRODUCTION OF SECONDARY AMINES

[75] Inventors: Arnold Hershman; Donald J. Bauer, both of Creve Coeur, Mo.

[73] Assignee: Monsanto Company, St. Louis, Mo.

[21] Appl. No.: 645,987

[22] Filed: Jan. 2, 1976

[51] Int. Cl.³ .................. C07C 85/11; C07C 87/28; C07C 135/02

[52] U.S. Cl. ..................... 564/384; 260/326.8; 562/555; 564/298; 564/299; 564/305; 564/462; 564/489

[58] Field of Search ............. 260/570.9, 583 R, 583 D, 260/584 R

[56] References Cited

U.S. PATENT DOCUMENTS

| 2,095,786 | 10/1949 | Andrews | 260/583 |
|---|---|---|---|
| 3,202,714 | 8/1965 | Zimmerer et al. | 260/584 |
| 3,316,299 | 4/1967 | Paquette | 260/583 |
| 3,414,616 | 12/1968 | Summers | 260/576 X |
| 3,856,795 | 12/1974 | Yardley | 260/576 X |

OTHER PUBLICATIONS

Houben–Weyl, "Methoden der Organischen Chemie," vol. 11, No. 2, pp. 190–204, (1958).

Mannich, "Archiv. der Pharmazie," vol. 254, pp. 349–363, (1916).

Houben–Weyl, "Methoden der Organischen Chemie," vol. 11, No. 1, pp. 516–519, (1957).

Primary Examiner—Robert V. Hines
Attorney, Agent, or Firm—Joseph D. Kennedy

[57] ABSTRACT

Tertiary amines such as alkyl or benzyl amines are catalytically oxidized by oxygen over an activated carbon catalyst to selectively produce secondary amines.

15 Claims, No Drawings

PRODUCTION OF SECONDARY AMINES

The present invention relates to a process for preparing secondary amines by catalytic oxidation of tertiary amines with oxygen over carbon catalyst to remove an alkyl or other similarly stable groups therefrom.

BACKGROUND OF THE INVENTION

It is known that certain tertiary amines can be treated with ozone to produce amine oxides and that under some conditions secondary amines are formed. A copending application of Applicant Arnold Hershman, Ser. No. 465,976, filed May 1, 1974, and now U.S. Pat. No. 3,969,398 concerns a process employing molecular oxygen-containing gas and activated carbon catalyst to remove an acetic acid group from N-phosphonomethylimino diacetic acid.

SUMMARY OF THE PRESENT INVENTION

The present invention concerns a process in which oxygen over carbon is employed to oxidize tertiary amines containing alkyl or other relatively stable groups to convert the tertiary amines to secondary amines in which a group has been removed and replaced by hydrogen. In general only one group is removed, so that the removal of the group produces the corresponding secondary amine, thereby providing a convenient and selective synthesis of such secondary amines.

DETAILED DESCRIPTION OF THE INVENTION

The process of the present invention can be illustrated:

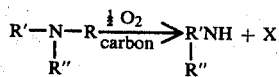

where R is alkyl, aralkyl, or hydroxyalkyl, and R' and R" are individually selected from R or aryl, or other hydrocarbyl, or any relatively stable substituent. The alkyl portion of the R group will generally be hydrocarbyl but can contain other substituents which do not appreciably affect the lability of the group to oxidative removal, especially when in a location remote from the nitrogen atom, such as halo, oxygen or sulfur, and can also contain additional amine groups, as in alkylene diamines, or the alkylene group can have two carbons attached to nitrogen to form a heterocyclic amine. X in the equation represents other cleavage products, which are generally an aldehyde formed from R, or its oxidation and decomposition products. The alkyl groups can be cycloalkyl groups, such as cyclohexyl, etc. The alkyl groups will generally be lower alkyl, such as 1 to 6 carbon atoms, but can be of longer chains such as up to 10 or more carbon atoms, and can be of branched or straight-chain structure. In the present invention it has been found that such unsubstituted alkyl groups as the ethyl group can be readily removed by use of carbon and oxygen in accord with the present invention. The benzyl and ethanol moieties were removable at rates comparable to or faster than that for ethyl. Extending the length of the carbon chains does not change the main characteristics of the groups, but some gradual increase in reactivity may occur. The methyl group may be somewhat more reactive than the ethyl. The groups to be removed will have at least one alpha-hydrogen, i.e. have a methyl, methylene, or methine group attached to the nitrogen and in general be selected so as to be more readily removed than other groups which are desired to be retained in the secondary amine. The phenyl group has been found very resistant to removal in the present process and the alkyl and similar groups described herein can conveniently be removed selectively from amines containing phenyl or other aryl groups. If the tertiary amine has groups of similar lability, a mixture of secondary amines will ordinarily be obtained, necessitating some product separation unless there is a use for the mixture. Amines which can be converted to secondary amines by the present process include, for example, triethylamine, tribenzylamine, tripropylamine, trihexylamine, N, N-diethyl-N-phenylamine, N-ethyl-N-,N-diphenylamine, N-ethyl-N-methyl-N-propylamine, N-benzyl-N,N-diphenylamine, tri-ethanol amine, tripropanolamine, N-cyclohexyl-N, N-diethylamine. It will be recognized that the tertiary amines can contain more than one amine group and still be operative and that the alkyl amines disclosed herein contemplate such amines, for example N,N,N',N',-tetraethyl-hexamethylene diamine. In such amines, the oxidation will ordinarily occur at both amine groups to convert both groups to secondary amine groups. Of course, if one or more of the amine groups is a secondary or primary amine group, as in N,N-diethylhexamethylene diamine, the oxidation will only occur at the tertiary amine group. Heterocyclic amines can be oxidatively cleaved, e.g. N-methylpyrollidine.

The present process involves the selective production of secondary amines, and the secondary amines are in general resistant to further cleavage reactions. The present process is effected by contacting described tertiary amines with oxygen in the presence of carbon. Preferred temperatures are in the range of about 75° C. to about 150° C., but lower or higher temperatures can be used, such as from ambient temperatures to about 250° C. or higher. The temperature affects the reaction rate with indications that, over preferred ranges, about a fifteen centigrade degree increase can be expected to cause a doubling of the reaction rate. The reaction rate also increases with increasing oxygen concentration. It appears that one-half an oxygen molecule is utilized for each organomethyl group cleaved. In practice, the amount of oxygen reacted will be from ½ to 1 or more moles oxygen for each mole of tertiary amine. Mild conditions of temperature and pressure are suitable for the reaction and can conveniently be employed, but higher pressures are also suitable, for example oxygen partial pressures from about 0.1 Kg/cm$^2$ to 100 or more Kg/cm$^2$. The total pressure in the reaction system will ordinarily be in the range from about ambient atmospheric pressure up to 200 Kg/cm$^2$ or higher, and oxygen can be supplied as such or in a molecular oxygen-containing gas. It has been found that oxygen partial pressures of from about 2 Kg/cm$^2$ to about 7 Kg/cm$^2$ can be conveniently employed and ordinarily give suitable reaction rates. Temperatures employed should be sufficient to initiate the reaction and to sustain the reaction once initiated, and temperatures sufficient to give desirable reaction rates will depend upon the catalyst and other reaction conditions, and upon the particular tertiary amine reactant.

The manner in which the tertiary amine is contacted with the molecular oxygen-containing gas and activated carbon can vary greatly. For example, the amine can be placed in a closed container with some free space containing molecular oxygen and shaken vigorously or agitated by stirring, or the molecular oxygen-containing gas can be bubbled through a solution of amine containing activated carbon, either through a straight tube or a tube with a fritted diffuser attached thereto. The contacting can also be accomplished in a tubular continuous reactor packed with activated carbon. Thus, the process of this invention can involve actively contacting the molecular oxygen-containing gas with an aqueous solution of the amine containing activated carbon catalyst. As those skilled in the art would realize, merely allowing a water solution of said amine containing said activated carbon to stand in contact with air under proper conditions would produce some of the desired product; however, the amount so produced would be small.

In conducting the process of this invention it is preferred to employ approximately saturated solutions of the tertiary amine in water at the temperature of reaction for ease of reaction and ease of recovery of the product. It is, of course, possible to employ very dilute, i.e., 0.1% amine in water; however, this results in a more difficult product recovery procedure. It is also possible to employ super-saturated solutions; however, the use of such solutions is usually not as desirable since the starting material could precipitate out during the reaction, thereby rendering the reaction process more difficult to conduct and separation of the product more difficult.

The reaction rate may be influenced to some extent by concentration of the amine, but suitable results can be obtained over broad ranges. The reaction can be conducted in solution, or can be conducted by contacting the amine with oxygen and carbon catalyst in the absence of solvent, preferably under conditions in which the amine is in liquid form. Water is a convenient and preferred solvent, but various other solvents can be used, e.g. glacial acetic acid, aqueous acetic acid, a mixture of acetic acid and acetic anhydride, etc., or various other solvents which are resistant to oxidation under the reaction conditions. Water is a suitable solvent, and ordinarily there is no reason to utilize other solvents unless effective in aiding solution of the amine reactant to facilitate the oxidation.

It is advisable to have the amine reactant in solution or other mobile, tractible form to facilitate the reaction. Some amines will be in liquid form under the reaction conditions and will need no solvent or similar component. While ordinarily the amine will be at least partially soluble in the reaction medium, it is also possible to conduct the reaction with a slurry, emulsion, or suspension of the amine in liquid medium. Illustrative of other solvents or liquids which can be employed are nitriles such as acetonitrile, propionitrile, benzonitrile, etc.; nitro compounds such as nitromethane, nitroethane, etc; halogenated hydrocarbons such as methylene chloride, ethylene chloride, carbon tetrachloride, etc.; and diemthylformamide and dimethylsulfoxide.

The acid-base character of the reaction medium appears to have some influence on the oxidation, but its effect on reaction rate varied with particular amines and the extent of conversion. The reaction, however, is operable over wide ranges of pH conditions, and there is no requirement to regulate this parameter, although there may be advantage on occasion in doing so. The pH of the reaction medium may vary from the presence of the amine reactant and carbon over ranges, for example, from 1 to 10 or so, and if desired acids such as hydrochloric or phosphoric can be employed as reaction medium, or bases such as sodium hydroxide. If desired, various salts or other materials may be present in the reaction medium, although ordinarily they will serve no useful purpose and may contribute to side reactions. Surfactants, such as emulsifying agents and the like, may possibly be used with advantage at times. Ordinarily for commercial practice it will not be desirable to select materials providing reactive halide or halogen, such as hydrochloric acid, because of the possible corrosive effect upon equipment, but the oxidation reaction is nevertheless operable in the presence of such materials.

By the term "molecular oxygen-containing gas", as employed herein, is meant any gaseous mixture containing molecular oxygen with one or more diluents which are non-reactive with the oxygen or with the reactant or product under the conditions of reaction. Examples of such gases are air, oxygen, oxygen diluted with helium, argon, nitrogen, or other inert gas, oxygen-hydrocarbon mixtures and the like. It is preferred to employ gases containing 20 or more percent by weight molecular oxygen and even more preferred to employ gases containing 90 or more percent by weight molecular oxygen. It is, of course, obvious to those of ordinary skill in the art that when molecular oxygen-containing gases containing other inert gases are employed, the pressures should be increased to maintain adequate partial pressures of oxygen in the system to maintain a sufficient rate of reaction.

The oxidation of some of the tertiary amines described herein may occur at appreciable rates without added catalyst, but such rates are markedly improved by activated carbon catalyst in accordance with the present invention. Any source or form of carbon can be used as a catalyst or substrate in the process of the present invention, for example powdered lampblack can be used and substantial reaction rates are obtainable. However, reaction rates are much better with activated carbons, which ordinarily have much higher surface areas than non-activated carbons, e.g. 551 m$^2$/gram for a particular activated carbon compared to 21 m$^2$/gram for a non-activated powdered lampblack.

The activated carbon catalysts employed in the process of this invention are well known in the art and are available under a large number of trade names. These activated carbons are characterized by high adsorptive capacity for gases, vapors and colloidal solids and relatively high specific surface areas. Carbon, char or charcoal is produced by destructive distillation of wood, peat, lignite, nut shells, bones, vegetable or other natural or synthetic carbonaceous matter, but must usually be "activated" to develop adsorptive power. Activation is usually achieved by heating to high temperatures (800°–900° C.) with steam or with carbon dioxide, which brings about a porous particle structure and increased specific surface area. In some cases hygroscopic substances, such as zinc chloride and/or phosphoric acid or sodium sulfate, are added prior to the destructive distillation or activation, to increase adsorptive capacity. The carbon content of active carbons ranges from about 10% for bone charcoal to about 98% for some wood chars and nearly 100% for activated carbons derived from organic polymers. The non-carbonaceous matter in activated charcoal will vary depending on precursor origin and/or activation procedure. For example, inorganic "ash" components containing aluminum and silicon are oftentimes present in large amounts accompanied by certain alkali metals and alkaline earths. The latter grouping influences the acidity-basicity characteristics of the activated carbon. Other inorganic constituents found in many activated carbons include iron and titanium. Depending on raw material origin and activation procedure, large amounts of oxygen can be present along with lesser amounts of hydrogen, nitrogen and sulfur. Oxygen content also influences activated carbon acidity-basicity.

The specific surface area of activated carbons, measured by the BET (Brunauer-Emmett-Teller) method using $N_2$, can range from 100 to nearly 2000 $m^2$/gram. The packed bulk density of activated carbons will depend on the porosity, form (powder vs. particulate) and also on the measuring technique employed. Measured values less than 0.15 g/cc and as high as about 0.6 g/cc for powders have been recorded. Particle or skeletal density, determined by mercury intrusion at atmospheric pressure, ranges from about 0.2 g/cc to about 0.53 g/cc on the same samples. Of course, density values on either side of the ranges are possible and it is understood that the values cited are for illustrative purposes and should not be construed as limiting the scope of the present invention.

The specific surface area of the activated carbon employed in the process of this invention will generally be in the range of from 100 to 2000 square meters per gram. It is preferred to employ activated carbons having a specific surface area of from 400 to 1600 square meters per gram.

The amount of granular or powdered activated carbon employed in the process of this invention can vary widely, ranging for example from 0.5 to 100 or more parts by weight for every 100 parts by weight of the amine employed. For the powdered activated carbons, it is preferred to employ from 5 to 100 parts by weight of activated carbon for each 100 parts by weight of the amine. For the activated carbons in granular forms, it is preferred to employ 10 to 200 parts by weight per 100 parts by weight of tertiary amine. It is, of course, obvious that in a tubular type continuous reactor, weight ratios of activated carbon to amine reactants can vary over even greater ranges then herein set forth.

The activated carbons employed in the process of this invention can be in the form of powders or granules, or various particulate forms or shapes, or as coatings on various substrates or structures.

In the powder form the activated carbons consist largely of material having a particle size finer than 325 mesh (about 45 microns or less in diameter)—although some larger particles may also be present. Particles as small as one micron have been observed by scanning electron microscopy. In the granular form, the particle size range can vary considerably. Particle sizes of 4×10 mesh, 8×30 mesh and 20×30 mesh are all available commercially and can be used. Mesh sizes given herein are those of the U.S. Standard Sieve Series.

The following is a listing of some of the activated carbons which are useful in the process of this invention. This listing is by way of example and is not an exhaustive listing. These activated carbons are for example:

| Trade Name | Sold by |
| --- | --- |
| Darco G-60 Spec. | ICI-America Wilmington, Delaware |
| Darco X | ICI-America Wilmington, Delaware |
| Norit SG Extra | Amer. Norit Co., Inc. Jacksonville, Fla. |
| Norit EN4 | Amer. Norit Co., Inc. Jacksonville, Fla. |
| Norit EXW | Amer. Norit Co., Inc. Jacksonville, Fla. |
| Norit A | Amer. Norit Co., Inc. Jacksonville, Fla. |
| Norit Ultra-C | Amer. Norit Co., Inc. Jacksonville, Fla. |
| Norit ACX | Amer. Norit Co., Inc. Jacksonville, Fla. |
| XZ | Barnebey-Cheney Columbus, Ohio |
| NW | Barnebey-Cheney Columbus, Ohio |
| JV | Barnebey-Cheney Columbus, Ohio |
| Bl. Pulv. | Pittsburgh Activated Carbon Div. of Calgon Corporation Pittsburgh, Pa. |
| PWA Pulv. | Pittsburgh Activated Carbon Div. of Calgon Corporation Pittsburgh, Pa. |
| PCB fines | Pittsburgh Activated Carbon Div. of Calgon Corporation Pittsburgh, Pa. |
| P-100 | No. Amer. Carbon, Inc. Columbus, Ohio |
| Nuchar CN | Westvaco Corporation Carbon Department Covington, Va. |
| Nucher C-1000N | Westvaco Corporation Carbon Department Covington, Va. |
| Nuchar C-190A | Wetsvaco Corporation Carbon Department Covington, Va. |
| Nuchar C-115A | Westvaco Corporation Carbon Department Covington, Va. |
| Code 1551 | Baker and Adamson Division of Allied |
| RB-111 | Amer. Norit Co., Inc. Jacksonville, Fla. |
| Norit 4 × 14 mesh | Amer. Norit Co., Inc. Jacksonville, Fla. |
| GI-9615 | Barnebey-Cheney Columbus, Ohio |
| VG-8408 | Barnebey-Cheney Columbus, Ohio |
| VG-8590 | Barnebey-Cheney Columbus, Ohio |
| NB-9377 | Barnebey-Cheney Columbus, Ohio |
| Grade 235 | Witco Chemical Corp. Activated Carbon Div. New York, New York |
| Grade 337 | Witco Chemical Corp. Activated Carbon Div. New York, New York |
| Grade 517 Activated Carbon Div. | Witco Chemical Corp. New York, New York |
| Grade 256 | Witco Chemical Corp. Activated Carbon Div. New York, New York |
| Columbia SXAC | Union Carbide New York, New York |

The following table gives the properties of a number of common activated carbons in powder form.

| POWDERS | | | | |
|---|---|---|---|---|
| Trade Name | Specific Surface Area (BET) m²/g | Pore Volume cc/g | Bulk Density g/cc | pH Water Solution |
| Darco G-60 | 1144 | 2.819 | .310 | 7.5 |
| Darco X | 296 | 1.555 | .440 | 5.0 |
| Norit SG Extra | 820 | 1.669 | .431 | 6.9 |
| Norit EXW | 1082 | 2.205 | .350 | 6.6 |
| Norit Ultra C | 1076 | 2.206 | .354 | 10.0 |
| Norit A | 900 | | .384 | 9.0 |
| Norit ACX | 1360 | | | 2.4 |
| Norit EN4* | 551–900 | | .401 | 7.0 |
| YZ | 1136 | 1.402 | .561 | 8.4 |
| NW | 662 | 1.405 | .482 | 11.4 |
| JV | 743 | 1.599 | .498 | 2.8 |
| Black-pulverized | 972 | 1.600 | .551 | 8.9 |
| PWA-pulverized | 898 | 1.641 | .520 | 8.2 |
| PCB-fines | 1010 | 1.502 | — | 10.1 |
| P-100 | 1394 | 2.500 | .383 | 2.5 |
| Nuchar CN | 963 | 4.537 | .178 | 7.1 |
| Nuchar C-1000N | 986 | 4.918 | .147 | 6.2 |
| Nuchar C-190A | 796 | 4.211 | .222 | 5.3 |
| Nuchar C-115A | 815 | 3.877 | .251 | 5.6 |
| Code 1551 | 458 | 2.310 | — | 3.4 |

Norit EN4*-Purchased from Fisher Scientific Company, Fairlawn, New Jersey.

The following list gives properties of some granular activated carbons.

| Trade Name | Mesh | Specific Surface Area m²/g | pH water | Particle Density g/cc |
|---|---|---|---|---|
| Norit RB 111 | 4 × 14 | 797 | 9.2 | 655 |
| Norit 4 × 14 mesh | 4 × 14 | 615 | 10.5 | .530 |
| GI 9615 | 8 × 14 | 1723 | 11.2 | .650 |
| VG-8408 | 6 × 10 | 670 | 9.2 | .837 |
| NB-9377 | 4 × 10 | 610 | 10.5 | .619 |
| Grade 235 | 4 × 10 | 1046 | 9.8 | .926 |
| Grade 235 | 8 × 30 | | | .918 |
| Grade 337 | 8 × 16 | | | |
| Grade 337 | 10 × 20 | | | |
| Grade 517 | 8 × 30 | | | |
| Grade 517 | 18 × 40 | | | |
| Grade 256 | 4 × 10 | 1130 | 9.9 | .788 |
| Columbia SXAC | 6 × 8 | 1245 | 7.1 | .747 |

The activated carbons used herein can be supported on other substrates, inert or otherwise. For example, suitable results are obtainable with a carbon on alumina catalyst which was prepared by decomposing butene at a temperature of about 450° C. over a ⅜ mesh activated alumina, the carbonaceous layer being substantially devoid of oxygenated compounds because prepared in inert atmosphere. A specific catalyst contained 30.47% by weight carbon.

In addition to the carbon, various other oxidation catalysts can be employed, particularly metallic catalysts such as various noble or base metals or their oxides. Such catalysts will ordinarily be utilized in known ways as dispersions or coatings on or impregnates on the carbon. In view of the effectiveness of carbon catalyst, there is generally no reason to employ metal or other generally more expensive catalysts, and the catalyst will consist essentially of carbon. However, noble metals are very effective oxidation catalysts for the reaction and can be employed along with the carbon. On a weight per weight basis, noble metals produce more rapid reaction rates than activated carbon, and hence there may at times be advantage in combining the noble metals, such as rhodium or palladium, with activated carbon. Such metals are, however, less readily available and more expensive, and therefore customarily used in lower concentraton in catalysts. Moreover, the noble metals tend to be leached out of carbon along with amine reactants or product in isolation or other procedures prior to recycling catalyst and other materials to a reactor, and this tends to negate any advantage in use of such materials. The noble metal catalysts for use herein can be prepared by various impregnation, precipitation and reduction procedures. For example carbon can be added to a solution of chloroplatinic acid, and sodium borohydride then slowly added, followed by dropwise addition of hydrochloric acid to obtain a slightly acidic pH. The amine reactant can then be added to the catalyst mixture. Other known ways of impregnating noble metals on substrates, as by absorption and decomposition of suitable salts, often followed by reduction can be employed.

EXAMPLE 1

Oxidations were carried out in a stainless steel 300 ml. autoclave reactor equipped with agitator and a bottom sampling valve. Reactor temperature was measured with an internal thermocouple and regulated with a temperature controller. The reactor could be operated with oxygen continually flowing, or dead-headed, and both procedures were demonstrated effective for oxidations described herein. The oxygen feed was through a dip tube with holes drilled in it for sparging. Pressure change in the reactor was measured versus a set load cell pressure, and recorded. In dead-head operation, the oxygen admission control valve was opened to admit oxygen to the desired pressure, usually after attaining desired operating temperature, and the valve was then closed. The reactor could then be repressured periodically by opening the control valve. For continuous flow, reactor pressure was controlled by a back pressure regulator on the exit line and an oxygen flow rate controller and valve on the inlet. In the continuous flow operation, the flow rate was generally 60 cc/minute (S.T.P.) of oxygen. The reaction was monitored by oxygen uptake, and analysis of off-gases for carbon dioxide, and by nuclear magnetic resonance analysis of periodic or final product samples. There was fairly good agreement with respect to the conversions determined by these different methods. Reactant and solvent were charged to the reactor. Catalyst was charged separately, such as powdered activated carbon, which was then employed in slurry form. The reactor was then brought to desired temperature and oxygen pressure. The procedure was carried out using about 1 gram Norit "A" activated carbon, triethylamine reactant, 3.3 grams (0.033 moles) and 100 ml water at 115° C., and 100 psi oxygen gauge pressure, using dead-head operation. A reaction time of about 6 hours gave a 40% conversion to diethylamine and triethylamine oxide. Nuclear magnetic resonance did not definitively distinguish between ethylamine and diethylamine, but failure to identify any primary amine product in related cleavage reactions indicates the product is diethylamine. No carbon dioxide was found and other cleavage fragments were acetic and formic acid. In place of the dead-head operation, continuous oxygen flow can be utilized with similar results, but continuous flow may be more appropriate when carbon dioxide is expected as one of the primary cleavage products and the oxygen flow would be useful in removing it from the reactor. Similar procedures with nitrilotripropionic acid gave 95 to 100% conversions in four to four and one-half hours and produced imino dipropionic acid, with the amine oxide of the nitrilotripropionic acid also being produced in one case, and carbon dioxide as an identified cleavage fragment.

EXAMPLE 2

Triethanol amine was oxidized in the reactor described in Example 1, using a continuous flow procedure. Five grams (0.033 mole) of the amine was used in 100 ml. water and about 1 gram Norit "A" activated carbon at a temperature of 115° C. and oxygen gauge pressure of 100 psi. In 5½ hours a 60% conversion was obtained, with the product being identified as diethanol amine, although not definitely distinguished from the primary amine. Formic acid was also identified. When a primary amine, hexamethylene diamine, was utilized under the same reaction conditions, no product was observed.

reaction period. No primary amine, benzyl amine, was present.

TABLE 1

Cleavage Reaction Rate
Reaction rate reported in g-moles reacted/hr-gm
of Norit "A" catalyst at 115° C. and 100 psi $O_2$ and
approximately 0.1 molar in tertiary amine (100 cc $H_2O$ solvent)

| Tertiary Amine | pH of Reaction Soln at Start of Run | Reaction Rate |
|---|---|---|
| $N(CH_2CH_2COOH)_3$ | 3.4 | 0.009–0.011 |
| $N(CH_2\text{-}\phi)_3$ | 2.0[1] | 0.004 |
| $N(CH_2CH_2OH)_3$ | 9.2 | 0.003–0.004 |
| $N(CH_2CH_2)_3$ | 10. | 0.001–0.002 |

[1]An acetic acid solvent.

Tribenzylamine was oxidized with variation in solvents and in some cases utilizing rhodium on carbon or palladium on carbon catalyst, or having a molecular sieve present in the reaction medium. Results are reported in Table 2.

TABLE 2

Oxidation of Tribenzylamine

| Run | Solvent | pH[1] Starting Amine in Solvent | Product Solution | Cumulative Reaction Time (min) | % Conv[2] | Products[3] |
|---|---|---|---|---|---|---|
| A. Variation of Solvent: 5.8 gms $N\text{—}(CH_2\text{—}\phi)_3$ reactant (0.020 moles) in solvent, 1.0 g Norit "A" as Catalyst | | | | | | |
| Operating Conditions: 115° C., 280 psi $N_2$ and 45 psi $O_2$ | | | | | | |
| A | 90 ml acetic acid + 10 ml water | 2.1 | 2.2 | 270 | 70 | $HN(CH_2\text{—}\phi)_2$ and $\phi\text{—}CHO$ |
| | | | | 390 | 35 | |
| B | 100 ml acetic acid | 2.0 | 2.2 | 260 | 60 | Same as A |
| C | 100 ml acetic acid + 7.4 gms Davison 3A Mole Sieve, Grade 564 8/12 M beads, dried @ 350° C. | — | — | 300 | 60 | Same as A |
| D | 100 ml acetic acid + 13.5 ml acetic anhydride (0.13 moles) | 2.2 | 2.1 | 280 | 65 | $CH_3C(O)N(CH_2\text{—}\phi)_2$[5] and $\phi\text{—}CHO$ |
| E | 100 ml acetic anhydride[4] | 4.4 | 4.3 | 330 | 5 | Same as D |
| B. Catalyst Studies - Use of Noble Metals: 5.8 g $N\text{—}(CH_2\text{—}\phi)_3$ reactant | | | | | | |
| Operating Conditions: 115° C., 280 psi $N_2$ and 45 psi $O_2$ | | | | | | |
| Solvent - 100 ml Acetic Acid | | | | | | |
| F | No catalyst | | | 300 | 0 | None detected |
| G | 1.0 g Norit "A" Activated Carbon | | | 260 | 60 | $HN(CH_2\text{—}\phi)_2$ and $\phi\text{—}CHO$ |
| Solvent - 90 ml Acetic Acid/10 ml $H_2O$ | | | | | | |
| H | 1.0 g Norit "A" Activated Carbon | | | 270 | 70 | Same Same as G |
| | | | | 390 | 85 | |
| I | 0.2 g 5% Rh/C (Lot 21,188 Engelhard) | | | 270 | 25 | Same as G |
| | | | | 330 | 30 | |
| J | 0.2 g 5% Pd/C (Lot 16,640 Engelhard) | | | 315 | 40 | Same as G |
| — | Assume 0.2 g Norit "A" and extrapolate from Run H | | | 270 | (14) | |
| | | | | 390 | (17) | |

FOOTNOTES FOR TABLE 2
[1]pH at 95° C. of (1) reactant tertiary amine in the solvent and (2) product solution at the end of the run.
[2]% Conversion estimated by proton nmr.
[3]All products positively identified by proton nmr. No primary amine present or other products detected.
[4]In acetic anhydride, the methylene nmr singlet of $N(CH_2\text{-}\phi)_3$ was considerably displaced from its position in the other solvents (−213 vs −265 to −268 cps). This is indicative of solvent-reactant interaction and may explain the slower rate in acetic anhydride.
[5]The product secondary amine was acylated to the N,N-amide by the acetic anhydride in the solvent systems.

EXAMPLE 3

Tribenzylamine was oxidized in accord with the procedure of Example 1 but with glacial acetic acid as solvent. The amine, 5.8 grams (0.02 mole) was utilized with the activated carbon catalyst and 100 ml solvent at 115° C. and 45 psi oxygen with 280 psi nitrogen. A 4½ hour reaction time gave a 60% conversion to product identified as dibenzylamine. Benzaldehyde was identified as a cleavage product, and no carbon dioxide was found. When triphenyl amine was substituted for tribenzylamine under essentially the same reaction conditions, no reaction or products were observed over a five hour In the procedures reported herein in which conversions are less than complete, the conversions can generally be improved by longer reaction times or higher reaction temperature or similar procedures, to obtain conversions better than 80 or 90%. Also, the failure in general to identify nitrogen containing side products in any substantial quantity indicates that yields of 80 to 90% or better of the desired secondary amine product are obtainable, and such selectivity is a significant aspect of the process. The selectivity is especially significant when the primary and secondary amines are similar in properties, such as boiling point and the like, and therefore difficult to separate by distillation or other common procedures. It will be noted that in some instances amine oxides are obtained along with secondary amines. Such amine oxides can be converted to secondary amines by thermal or other procedures, thereby in effect increasing the yield of secondary amines. It is advantageous that the present oxidation process can be conducted under relatively mild conditions using a readily available oxidizing agent, oxygen, available from air or other sources, and a material available in commercial supply, activated carbon, as catalyst. In view of its effectiveness, relatively low cost, and apparent resistance to inactivation and suitability for recycling, the catalyst will usually consist essentially of activated carbon. However, if desired, the catalyst can comprise activated carbon and noble metal.

The secondary amines obtained by the present process in general constitute a known class of amines of recognized industrial utility as bases, detergents or materials useful in preparing detergents, agents or intermediates therefor for use in rubber compounding, reactants for acylation, etc.

The specific procedures set forth herein are for illustration, and it will be recognized that other reactant amines and catalysts can be used in the procedures, and that the conditions of the procedures can vary. Thus, for example, dibenzylphenylamine and benzylethylphenylamine can be utilized as reactants in Example 1 to obtain cleavage to secondary amines. Since the phenyl group is resistant to cleavage in the present process, the process may be particularly useful in converting various amines with phenyl and other N-substituents i.e. disubstituted anilines, to secondary anilines. The tertiary amines utilized can contain two or three different groups attached to nitrogen, or three identical groups can be attached. Tertiary amines with three identical groups may be more commonly available and their use avoids the possibility of obtaining mixtures of secondary amines due to competitive removal of different groups, although such mixtures are often useful and, moreover, predominant production of a single secondary amine may occur if there is sufficient difference in cleavage rates when different groups are attached. Other catalysts can be employed with good results in the procedure of Example 1, viz. Nuchar CN and Durco X, and a carbon-on-alumina catalyst prepared by decomposition of butene over an alumina catalyst. Similar results can also be obtained with 5% by weight Rh on carbon, 5% by weight Rh on alumina (KA-101) catalysts, or with other noble metals on carbon, alumina or other catalyst supports, for example 5% by weight Pd on alumina, or Pt or Ru or other noble metal oxidation catalysts.

What is claimed is:

1. A process for the production of secondary amines which comprises contacting a tertiary amine with oxygen and carbon at a temperature sufficient to oxidize the amine and effect removal of a group attached to the nitrogen thereof, the temperature being in the range of ambient temperatures up to about 250° C., the group being selected from the class consisting of alkyl, aralkyl and hydroxyalkyl, and in which the other groups on the nitrogen are selected from the aforesaid class or groups relatively more stable to oxidative removal than the aforesaid class, and obtaining the resulting secondary amine in substantial yield.

2. A process in accord with claim 1 in which the tertiary amine is represented by the formula:

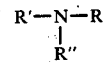

where R is selected from alkyl, aralkyl or hydroxylalkyl, and R' and R" are individually selected from R or monovalent hydrocarbyl.

3. The process of claim 1 in which a trialkyl amine is converted to a dialkylamine.

4. The process of claim 1 in which a trialkanol amine is converted to a dialkanol amine.

5. The process of claim 1 in which a triaralkylamine is converted to a diaralkylamine.

6. The process of claim 1 in which an activated carbon catalyst is employed.

7. The process of claim 1 in which a lower alkyl group is removed from the tertiary amine.

8. The process of claim 1 wherein activated carbon catalyst is employed at pressure above atmospheric and at temperatures in the range of about 75° C. to about 150° C.

9. The process of claim 1 wherein the oxidation is conducted in a solvent employing activated carbon catalyst and a molecular oxygen containing gas at about 75° C. to about 150° C.

10. The process of claim 9 in which the partial oxygen pressure is in the range of about 2 Kg/cm$^2$ to about 7 Kg/cm$^2$.

11. The process of claim 1 wherein a catalyst consisting essentially of activated carbon is employed.

12. The process of claim 1 wherein a catalyst comprising activated carbon and noble metal is employed.

13. The process of claim 1 in which the tertiary amine contains three identical groups attached to the nitrogen.

14. The process of claim 1 in which oxidation is conducted in aqueous solution.

15. The process of claim 1 in which oxidation is conducted in acetic acid.